United States Patent [19]

Harigaya et al.

[11] Patent Number: 4,596,826

[45] Date of Patent: Jun. 24, 1986

[54] CARBOXYLIC ACID AMIDE COMPOUNDS AND THEIR DERIVATIVES

[75] Inventors: Yasuji Harigaya, Chiba; Hiroo Ogura; Mitsuo Mihara, both of Ibaraki; Motosuke Yamanaka, Chiba; Kiyomi Yamatsu, Kanagawa, all of Japan

[73] Assignee: Eisai Co., Ltd., Tokyo, Japan

[21] Appl. No.: 620,050

[22] Filed: Jun. 12, 1984

[30] Foreign Application Priority Data

Jun. 14, 1983 [JP] Japan ................. 58-104873

[51] Int. Cl.⁴ ................. C07C 101/453; A61K 31/195
[52] U.S. Cl. ..................... 514/563; 562/455; 562/442; 548/513; 514/417
[58] Field of Search ............... 562/455, 456, 457, 442; 514/563, 417; 548/513

[56] References Cited

U.S. PATENT DOCUMENTS

| | | | |
|---|---|---|---|
| 3,507,904 | 4/1970 | Schwartz et al. | 562/457 |
| 3,654,302 | 4/1972 | Schwartz et al. | 548/513 |
| 3,745,170 | 7/1973 | Fujinami et al. | 548/513 |
| 3,987,056 | 10/1976 | Cobb | 548/513 |
| 4,002,460 | 1/1977 | Pallos | 562/442 |
| 4,361,576 | 11/1982 | Buhler et al. | 548/513 |
| 4,409,018 | 10/1983 | Ishida | 548/513 |

*Primary Examiner*—James H. Reamer
*Attorney, Agent, or Firm*—Wenderoth, Lind & Ponack

[57] ABSTRACT

Described herein are novel carboxylic acid amide compounds or carboximide compounds represented by the general formula:

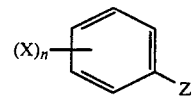

wherein Z represents a group of the formula (1) or (2):

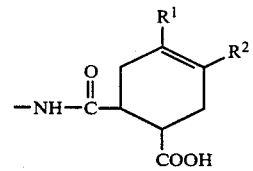

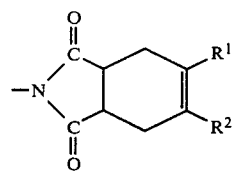

wherein $R^1$ and $R^2$ are hydrogen atom or methyl group, respectively; Xs, which may be the same or different, are hydrogen atom, a lower alkyl, lower alkoxy, halo, or alkyl halide group, respectively, and n represents an integer of 0 to 2, and their pharmaceutically acceptable salts; process for the production thereof; and medicines containing the same. The novel compounds are useful as treating, preventing and improving agents for diseases attended with cerebral dysfunction as well as various symptoms caused by the said diseases. Further, the compounds are useful for the improvement of neurosis of the stomach; and treatment and prevention for various constipation.

16 Claims, No Drawings

CARBOXYLIC ACID AMIDE COMPOUNDS AND THEIR DERIVATIVES

The present invention relates to novel carboxylic acid amide compounds or carboximide compounds having excellent activities as medicines, to processes for their production and to medicines containing the same.

More particularly, this invention relates to carboxylic acid amide compounds or carboximide compounds represented by the general formula (I):

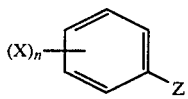

wherein Z represents a group of the formula (1):

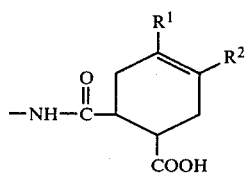

wherein $R^1$ and $R^2$ are hydrogen atom or methyl group, respectively, or a group of the formula (2):

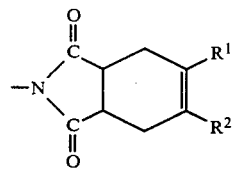

wherein $R^1$ and $R^2$ are hydrogen atom or methyl group, respectively;

Xs, which may be the same or different, are hydrogen atom, a lower alkyl, lower alkoxy, halo, or alkyl halide group, respectively;

and n represents an integer of 0 to 2, and the salts thereof; to process for their production; and to medicines containing the same.

As used in the present invention, the term "salts" denotes a pharmaceutically acceptable salt, and the salts includes Na, K, Ca and Mg salts, for example.

The carboxylic acid amide compounds provided by the present invention are novel compounds which have not yet been disclosed in any literature, and it has now been discovered that these compounds have excellent antispasmodic, anti-hypoxic, anti-anxious and sedative activities, and therefore, are useful as treating, preventing and improving agents for diseases such as epilepy, cerebral vascular lesion sequelae, cephalic trauma sequelae, attended with convulsion, and in addition, are useful as treating, preventing and improving agents for various symptoms caused by diseases, which are attended with cerebral dysfunction such as epilepsy, cerebrovascular diseases sequelae, head injury sequelae and the like, the said symptoms including convulsion, disturbance of consciousness, impaired memory or disturbance of movement.

Further, the carboxylic acid amide compounds provided by the present invention show excellent activities to motility of alimentary canal, and normalization effect to lesion of motile faculty over the whole digestive organs, and enhancing effect on the digestive function. Therefore, the compounds of the present invention are useful as regulators for motile faculty of digestive organ function as medicines based on the above effects. More specifically, the compounds of the present invention are useful, for instance, for the improvement of neurosis of gastrointestin, subjective symptom such as ileus, diverticulum, sequelae of gastrectomy, abdominal pain accompanied by lesion of gastrointestinal function in postoperation, nausea, vomiting, abdominal discomfort, abdominal enlargement, loss of appetite, and the like; and treatment and prevention for various constipation such as generous constipation, diabetic constipation, aged constipation, autonomic nervous ataxia, etc., by virtue of pharmacological activities which accelerate the normality of motility of stomach and motility of subordinate alimentary canal lying on lower portions than the duodenums.

The present inventors have discovered that these compounds unexpectedly have the above mentioned excellent activities, and have thus accomplished the present invention.

It is therefore an object of the present invention to provide novel compounds which are useful as medicines such as treating, preventing and improving agents for diseases including epilepsy, cerabral vascular lesion sequelae, cephalic trauma sequelae, attended with convulsion; treating, preventing and improving agents for clouding of consciousness, defect of memory and failure of muscular coordination due to these diseases; antiulcertive drugs; and regurator for gastrointestinal function.

It is another object of the present invention to provide processes for the production of novel compounds useful as such medicines.

It is a further object of the present invention to provide novel treating, preventing and improving agents for diseases such as epilepsy, cerebral vascular lesion sequelae, cephalic trauma sequelae, attended with convulsion; and treating, preventing and improving agents for various symptoms caused by diseases, which are attended with cerebral dysfunction such as epilepsy, cerebrovascular diseases sequelae, head injury sequelae and the like, the said symptoms including convulsion, disturbance of consciousness, impaired memory or disturbance of movement; and regurator for gastrointestinal function.

The compounds (I) of the present invention can be produced by various routes, among which some representative examples commonly employed are described below:

(1) Where Z in the formula (I) represents a group of the formula:

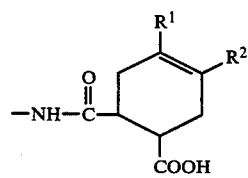

wherein $R^1$ and $R^2$ are hydrogen atom or methyl group, respectively,

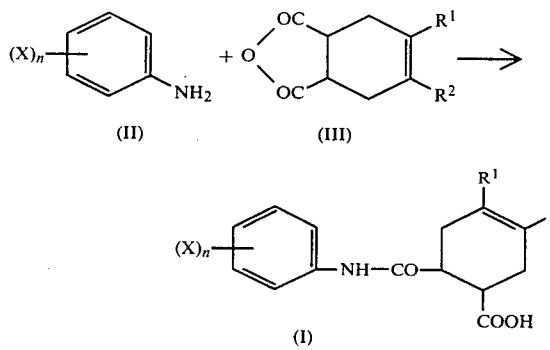

that is, an aniline compound of the formula (II) is reacted with a carboxylic anhydride of the formula (III) in a conventional manner to provide a desired compound (I). In this case, the reaction is conducted under a heating condition, usually at room temperature or a temperature of about 150° C. or less, and in a solvent such as, for example, benzene, chloroform, toluene, isopropyl ether, and acetonitrile.

(2) Where Z in the formula (I) represents a group of the formula:

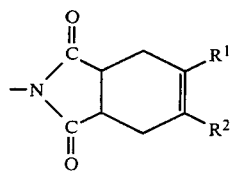

wherein $R^1$ and $R^2$ are as defined above, in other words, where the compound (I) is a carboxylic acid amide compound, the carboxylic acid amide compound (I), for example, produced in the process (1), is dehydrated by heating to a temperature of 180° to 220° C. in the absence of solvent, or refluxed with thionyl chloride added thereto for a several time in a non-protonic solvent such as benzene and toluene. After the completion of reaction, the solvent is evaporated off to provide a crude imide compound.

(3) Where Z in the compound of the present invention represents a group of the formula:

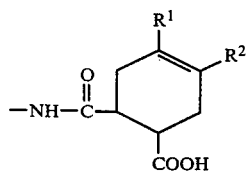

wherein $R^1$ and $R^2$ are as defined above, in other words, where the compound of the present invention is a carboxylic acid amide compound, it can be easily converted into the pharmaceutically acceptable salt thereof. The representative salts include alkali or alkaline earth metal salts such as Na, K, Ca and Mg salts.

A metal salt of the compound may be produced by, for example, the following processes.

A sodium salt of the compound can be produced by adding to a corresponding amide carboxylic acid, an equivalent mol of sodium hydroxide.

Likely, another alkali or alkaline earth metal salt of the compound can also be obtained using a corresponding hydroxide or oxide. Alternatively, it can be produced by dissolving a sodium or potassium amide carboxylate in water, and then adding another metal chloride thereinto for substitution.

Representative compounds of the present invention are illustrated below, but it should be understood that the present invention is not restricted thereto.

Furthermor, although all the compounds set forth below are expressed in free forms, it should of course be understood that they include pharmaceutically acceptable salts thereof as mentioned above.

6-(phenyl-aminocarbonyl)-3,4-dimethyl-3-cyclohexene carboxylic acid 6-(phenyl-aminocarbonyl)-3-methyl-3-cyclohexene carboxylic acid 6-(phenyl-aminocarbonyl)-4-methyl-3-cyclohexene carboxylic acid 6-(4-tolyl-aminocarbonyl)-3,4-dimethyl-3-cyclohexene carboxylic acid 6-(4-tolyl-aminocarbonyl)-3-methyl-3-cyclohexene carboxylic acid 6-(4-tolyl-aminocarbonyl)-4-methyl-3-cyclohexene carboxylic acid 6-[(3,5-bistrifluoromethyl phenyl)-aminocarbonyl]-3,4-dimethyl-3-cyclohexene carboxylic acid 6-[(3,5-bistrifluoromethyl phenyl)-aminocarbonyl]-3-methyl-3-cyclohexene carboxylic acid 6-[(3,5-bistrifluoromethyl phenyl)-aminocarbonyl]-4-methyl-3-cyclohexene carboxylic acid 6-[(3,5-dimethylphenyl)-aminocarbonyl]-3,4-dimethyl-3-cyclohexene carboxylic acid 6-[(3,5-dimethylphenyl)-aminocarbonyl]-3-methyl-3-cyclohexene carboxylic acid 6-[(3,5-dimethylphenyl)-aminocarbonyl]-4-methyl-3-cyclohexene carboxylic acid 6-[(4-chlorophenyl)-aminocarbonyl]-3,4-dimethyl-3-cyclohexene carboxylic acid 6-[(4-chlorophenyl)-aminocarbonyl]-3-methyl-3-cyclohexene carboxylic acid 6-[(4-chlorophenyl)-aminocarbonyl]-4-methyl-3-cyclohexene carboxylic acid 6-[(3-trifluoromethylphenyl)-aminocarbonyl]-3,4-dimethyl-3-cyclohexene carboxylic acid 6-[(3-trifluoromethylphenyl)-aminocarbonyl]-3-methyl-3-cyclohexene carboxylic acid 6-[(3-trifluoromethylphenyl)-aminocarbonyl]-4-methyl-3-cyclohexene carboxylic acid 6-[(3,5-dichlorophenyl)-aminocarbonyl]-3,4-dimethyl-3-cyclohexene carboxylic acid 6-[(3,5-dichlorophenyl)-aminocarbonyl]-3-methyl-3-cyclohexene carboxylic acid 6-[(3,5-dichlorophenyl)-aminocarbonyl]-4-methyl-3-cyclohexene carboxylic acid 6-[(3-chlorophenyl)-aminocarbonyl]-3,4-dimethyl-3-cyclohexene carboxylic acid 6-[(3-chlorophenyl)-aminocarbonyl]-3-methyl-3-cyclohexene carboxylic acid 6-[(3-chlorophenyl)-aminocarbonyl]-4-methyl-3-cyclohexene carboxylic acid 6-[(4-n-propylphenyl)-aminocarbonyl]-3,4-dimethyl-3-cyclohexene carboxylic acid 6-[(4-n-propylphenyl)-aminocarbonyl]-3-methyl-3-cyclohexene carboxylic acid 6-[(4-n-propylphenyl)-aminocarbonyl]-4-methyl-3-cyclohexene carboxylic acid 6-[(4-methoxy phenyl)-aminocarbonyl]-3,4-dimethyl-3-cyclohexene carboxylic acid 6-[(4-methoxy phenyl)-aminocarbonyl]-3-methyl-3-cyclohexene carboxylic acid
6-[(4-methoxy phenyl)-aminocarbonyl]-4-methyl-3-cyclohexene carboxylic acid
6-[(2-chloro-5-trifluoromethylphenyl)-aminocarbonyl]-3,4-dimethyl-3-cyclohexene carboxylic acid
6-[(2-chloro-5-trifluoromethylphenyl)-aminocarbonyl]-3-methyl-3-cyclohexene carboxylic acid
6-[(2-chloro-5-trifluoromethylphenyl)-aminocarbonyl]-4-methyl-3-cyclohexene carboxylic acid
6-[(2-methyl-4-chlorophenyl)-aminocarbonyl]-3,4-dimethyl-3-cyclohexene carboxylic acid
6-[(2-methyl-4-chlorophenyl)-aminocarbonyl]-3-methyl-3-cyclohexene carboxylic acid
6-[(2-methyl-4-chlorophenyl)-aminocarbonyl]-4-methyl-3-cyclohexene carboxylic acid
6-[(3-ethylphenyl)-aminocarbonyl]-3,4-dimethyl-3-cyclohexene carboxylic acid
6-[(3-ethylphenyl)-aminocarbonyl]-3-methyl-3-cyclohexene carboxylic acid
6-[(3-ethylphenyl)-aminocarbonyl]-4-methyl-3-cyclohexene carboxylic acid
6-[(4-bromophenyl)-aminocarbonyl]-4-methyl-3-cyclohexene carboxylic acid
6-[(4-bromophenyl)-aminocarbonyl]-3,4-dimethyl-3-cyclohexene carboxylic acid
6-[(4-n-butylphenyl)-aminocarbonyl]-3,4-dimethyl-3-cyclohexene carboxylic acid
6-[(4-n-butylphenyl)-aminocarbonyl]-3-methyl-3-cyclohexene carboxylic acid
6-[(2-chlorophenyl)-aminocarbonyl]-3,4-dimethyl-3-cyclohexene carboxylic acid
6-[(2-chlorophenyl)-aminocarbonyl]-3-methyl-3-cyclohexene carboxylic acid
6-[(2-chlorophenyl)-aminocarbonyl]-4-methyl-3-cyclohexene carboxylic acid
6-[(2-tolyl)-aminocarbonyl]-3,4-dimethyl-3-cyclohexene carboxylic acid
6-[(2-tolyl)-aminocarbonyl]-3-methyl-3-cyclohexene carboxylic acid
6-[(2-tolyl)-aminocarbonyl]-4-methyl-3-cyclohexene carboxylic acid
N-(phenyl)-4-methyl-4-cyclohexene-1,2-dicarboximide
N-(phenyl)-4,5-dimethyl-4-cyclohexene-1,2-dicarboximide
N-(3-chlorophenyl)-4-methyl-4-cyclohexene-1,2-dicarboximide
N-(3-chlorophenyl)-4,5-dimethyl-4-cyclohexene-1,2-dicarboximide
N-(4-chlorophenyl)-4-methyl-4-cyclohexene-1,2-dicarboximide
N-(4-chlorophenyl)-4,5-dimethyl-4-cyclohexene-1,2-dicarboximide
N-(3-trifluoromethylphenyl)-4,5-dimethyl-4-cyclohexene-1,2-dicarboximide
N-(3-trifluoromethylphenyl)-4-methyl-4-cyclohexene-1,2-dicarboximide
N-(3-trifluoromethylphenyl)-4,5-dimethyl-4-cyclohexene-1,2-dicarboximide
N-(3,5-dimethylphenyl)-4-methyl-4-cyclohexene-1,2-dicarboximide
N-(3,5-dimethylphenyl)-4,5-dimethyl-4-cyclohexene-1,2-dicarboximide
N-(3,5-dichlorophenyl)-4-methyl-4-cyclohexene-1,2-dicarboximide
N-(3,5-dichlorophenyl)-4,5-dimethyl-4-cyclohexene-1,2-dicarboximide
N-(3,5-bistrifluoromethylphenyl)-4-methyl-4-cyclohexene-1,2-dicarboximide
N-(3,5-bistrifluoromethylphenyl)-4,5-dimethyl-4-cyclohexene-1,2-dicarboximide
N-(4-tolyl)-4,5-dimethyl-4-cyclohexene-1,2-dicarboximide
N-(4-tolyl)-4-methyl-4-cyclohexene-1,2-dicarboximide
N-(3,5-dimethylphenyl)-4,5-dimethyl-4-cyclohexene-1,2-dicarboximide
N-(3,5-dimethylphenyl)-4-methyl-4-cyclohexene-1,2-dicarboximide
N-(4-n-propylphenyl)-4,5-dimethyl-4-cyclohexene-1,2-dicarboximide
N-(4-n-propylphenyl)-4-methyl-4-cyclohexene-1,2-dicarboximide
N-(4-methoxyphenyl)-4,5-dimethyl-4-cyclohexene-1,2-dicarboximide
N-(4-methoxyphenyl)-4-methyl-4-cyclohexene-1,2-dicarboximide
N-(2-chloro-5-trifluoromethylphenyl)-4,5-dimethyl-4-cyclohexene-1,2-dicarboximide
N-(2-chloro-5-trifluoromethylphenyl)-4-methyl-4-cyclohexene-1,2-dicarboximide
N-(2-methyl-4-chlorophenyl)-4,5-dimethyl-4-cyclohexene-1,2-dicarboximide
N-(3-ethylphenyl)-4,5-dimethyl-4-cyclohexene-1,2-dicarboximide
N-(4-bromophenyl)-4-methyl-4-cyclohexene-1,2-dicarboximide
N-(2-methyl-4-chlorophenyl)-4-methyl-4-cyclohexene-1,2-dicarboximide
N-(3-ethylphenyl)-4-methyl-4-cyclohexene-1,2-dicarboximide
N-(4-bromophenyl)-4,5-dimethyl-4-cyclohexene-1,2-dicarboximide
N-(2-tolyl)-4,5-dimethyl-4-cyclohexene-1,2-dicarboximide
N-(2-tolyl)-4-methyl-4-cyclohexene-1,2-dicarboximide
N-(2-chlorophenyl)-4,5-dimethyl-4-cyclohexene-1,2-dicarboximide
N-(2-chlorophenyl)-4-methyl-4-cyclohexene-1,2-dicarboximide In order to explain the effect of the present invention in more detail, experimental examples are given below.

EXPERIMENT 1

(1) Maximum electro-shock convulsion resistant activity

This was examined using STD-ddy type mice (weighing 20 to 30 g) by the method of Goodman, et al. [GOODMAN (L. S), SINGGREWALD (M.), BROWN (V. C.) and SWINYARD (E. A.), Am. J. of Pharmacol. and Ther., (1953), 168–175]. That is, a compound to be tested was administered into mice, and after two hours, a physiological aqueous saline solution was dropped into both eyes of each the mice. The mice were allowed to undergo an electric shock (25 mA, 0.25 sec)in an electric shock convulsion device (made by Unique Medical), with their corneas being placed in contact with the twin-electrode thereof. Thus, the tonic stretch action which might be caused thereby was observed whether to be present or not in the mice. Eight mice were used for every one group. As test compounds, there were selected the following compounds: 6-[(3,5-bistrifluoromethylphenyl)-aminocarbonyl]-3,4-dimethyl-3-cyclohexene carboxylic acid (compound A), and 6-[(3,5-bistrifluoromethylphenyl)-aminocarbonyl]-3(4)-methyl-3-cyclohexene carboxylic acid (compound B).

Upon the experiment, both the compounds A and B, orally administered into the eight mice in dosage of 320 mg/kg, showed inhibition activities in all the eight mice.

(2) Anti-metrazol

A test compound was administered into STD-ddY type mice (weighing 20 to 30 g), and after 90 minutes, metrazol was intraabdominally administered into the mice in a dosage of 150 mg/kg. The mice were observed for 15 minutes whether to be dead or not due to convulsion. Five mice were used for every one group. In addition to the above compounds A and B as test compounds, there were selected the followng compounds: 6-[(3,5-dichlorophenyl)-aminocarbonyl]-3(4)-methyl-cyclohexene carboxylic acid (compound C), and 6-[(3,5-dimethylphenyl)-aminocarbonyl]-3(4)-methyl-3-cyclohexene carboxylic acid (compound D). The inhibition (%) of metrazol-induced lethality was 100% with the compound C, 60% with the compound D, and 40% with the compounds A and B, orally administered in a dosage of 300 mg/kg, respectively.

EXPERIMENT 2

(1) Increase of duodenal motility

S. D. rats weighing about 300 g were deprived of food for over night. Under ether anesthesia, a rubber balloon and open-tip catheter was inserted into the stomach and duodenum, respectivelly. Changes in gastrointestinal motility was recorded by connecting the tip of balloon and catheter to a pressure transducer.

As test compounds, compounds A and B were selected. These compounds show increase of the duodenal motility in a dose of 20 mg/kg(i.v.).

(2) Gastrointestinal motility in anesthetized beagles

Adult beagles weighing about 10 kg were used in this experiments. Under urethane-morphine anesthesia, force transducer was set onto the serosal surface of gastric body, duodenum, jejunum and colon. Variations of contractibility were continuously recorded by connecting the transducer to a amplifier.

Tested compound A up to 10 mg/kg(i.d.) accelerated the duodenal, jejunal and colonic motility.

As in the above results, the compounds of the present invention have excellent anti-spasmodic and anti-hypoxic activities, and can be thus anticipated to have tranquilization activity. It can therefore be understood that they are effective as treating, preventing and improving agents for diseases such as epilepsy, cerebral vascular lesion sequelae and cephalic trauma sequelae, attended with convulsion.

The compounds of the present invention are those having a lower toxicity a high safety, and hence, can be administered continuously over a long period. Even in this sense, the present invention is high in utility value.

More particularly, 6-[(3,5-bistrifluoromethylphenyl)-aminocarbonyl]-3,4-dimethyl-3-cyclohexene carboxylic acid, the typical compound of the present invention shows $LD_{50}$ 1,512 mg/kg in male rat, and $LD_{50}$ 1,121 mg/kg in female rat.

In administering the compounds of the present invention of the above-mentioned diseases, although the dosage varies widely, depending on the kind of disease, the severity of the condition of patient, the type of compound and the age of patient, it may be in the range of about 10 mg to 1,000 mg, preferably about 50 mg to 300 mg, per day for a human adult in oral or parenteral administeration. For preparations of the compounds of the present invention, they may be made in the form of, for example, powders, granules, particulates, tablets, capsules and injectable compositions, using usual carriers, in accordance with the conventional pharmaceutical practice.

More specifically, for preparing oral solid preparations, the main drug is mixed with an excipient and further, if necessary, a binder, disintegrator, lubricants, colorants, flavoring agents, etc., and then formed into tablets, coated tablets, particulates, powders, capsules, etc., in the conventional manner.

As the excipients, there can be used, for example, lactose, corn starch, white sugar, glucose, sorbitol, crystalline cellulose, silicon dioxide, etc. As the binders, there can be used, for example, polyvinyl alcohol, polyvinyl ether, ethyl cellulose, methyl cellulose, gum arabic, tragacanth, gelatin, shellac, hydroxypropyl cellulose, hydroxypropyl starch, polyvinylpyrrolidone, etc. As the disintegrators, there can be used, for example, starch, agar, gelatin powder, crystalline cellulose, calcium carbonate, sodium bicarbonate, calcium citrate, dextrin, pectin, etc. As the lubricants, there can be used, for example, magnesium stearate, talc, polyethylene glycol, silica, hardened vegetable oils, etc. As the colorants, there can be used those allowed as additives to medicines. As the flavoring agents, there can be used cocoa powders, menthol, aromatic acids, mint oil, camphol, cinnamon powder, etc. These tablets, particulates etc. may of course be suitably coated with sugar, gelatin or the like, if necessary.

For preparing an injectable solution, the main drug is mixed with a pH adjusting agent, buffer, stabilizer, solubilizing agent, etc., if necessary and made into compositions for subcutaneous, intramuscular, intravenous injections in the conventional manner.

A preparation example is given below which contains, as an active ingredient, 6-[(3,5-dichlorophenyl)-aminocarbonyl]-3,4-dimethyl-3-cyclohexene carboxylic acid (which will be referred to as a main drug hereinafter) which is a representative compound of the compounds according to the present invention.

PREPARATION EXAMPLE (TABLET)

Main drug: 10 g
Crystallin cellulose: 90 g
Corn starch: 66 g
Hydroxypropyl cellulose: 10 g
Magnecium stearate: 4 g The mixture consisting of the above components was formed into tablets (each weighing 180 mg) in the conventional manner by the above-mentioned prescription.

The present invention is further illustrated by way of the following examples, which are on no account intended to limit the present invention.

EXAMPLE 1

6-(phenyl-aminocarbonyl)-3,4-dimethyl-3-cyclohexene carboxylic acid 0.9 g (0.01 mol) of aniline was reacted with 1.8 g (0.01 mol) of 3,4-dimethyl-3-cyclohexene dicarboxylic anhydride under reflux for 4 hours in isopropyl ether. The reaction mixture was cooled, and the precipitated crystals were filtered off to provide 2.6 g (yield: 96%) of the title compound.

Melting point: 155°–156° C.
Elemental analysis: for $C_{16}H_{19}NO_3$

|  | C | H | N |
|---|---|---|---|
| Calculated (%): | 70.29 | 7.02 | 5.12 |
| Found (%): | 70.43 | 6.98 | 5.16 |

EXAMPLE 2

6-(4-tolyl-aminocarbonyl)-3,4-dimethyl-3-cyclohexene carboxylic acid

Using as starting materials, 1.1 g (0.01 mol) of p-toluidine and 1.8 g (0.01 mol) of 3,4-dimethyl-3-cyclohexene carboxylic acid, the reaction was carried out in the same manner as in Example 1 to provide 2.7 g (yield: 95%) of the title compound.
Melting point: 174°–176° C. (decomposition)
Elemental analysis: for $C_{17}H_{21}NO_3$

|  | C | H | N |
|---|---|---|---|
| Calculated (%): | 71.04 | 7.38 | 4.87 |
| Found (%): | 71.01 | 7.38 | 4.86 |

EXAMPLE 3

The following compounds were obtained by the procedure similar to that of Example 1.

6-[(3,5-dimethylphenyl)-aminocarbonyl]-3,4-dimethyl-3-cyclohexene carboxylic acid
Melting point: 177° C. (decomposition)
Elemental analysis: for $C_{18}H_{23}NO_3$

|  | C | H | N |
|---|---|---|---|
| Calculated (%): | 71.72 | 7.70 | 4.64 |
| Found (%): | 71.74 | 7.22 | 4.72 |

6-[(4-chlorophenyl)-aminocarbonyl]-3,4-dimethyl-3-cyclohexene carboxylic acid
Melting point: 180° C. (decomposition)
Elemental analysis: for $C_{16}H_{18}NO_3Cl$

|  | C | H | N |
|---|---|---|---|
| Calculated (%): | 62.43 | 5.90 | 4.55 |
| Found (%): | 62.48 | 5.81 | 4.69 |

6-[(3,5-bistrifluoromethylphenyl)-aminocarbonyl]-3,4-dimethyl-3-cyclohexene carboxylic acid
Melting point: 168°–169° C.
Elemental analysis: for $C_{18}H_{17}NO_3F_6$

|  | C | H | N |
|---|---|---|---|
| Calculated (%): | 52.80 | 4.19 | 3.42 |
| Found (%): | 52.79 | 4.19 | 3.43 |

6-[(3-trifluoromethylphenyl)-aminocarbonyl]-3,4-dimethyl-3-cyclohexene carboxylic acid
Melting point: 187°–188° C. (decomposition)
Elemental analysis: for $C_{17}H_{18}NO_3F_3$

|  | C | H | N |
|---|---|---|---|
| Calculated (%): | 59.81 | 5.32 | 4.10 |
| Found (%): | 59.86 | 5.33 | 4.03 |

6-[(3,5-dichlorophenyl)-aminocarbonyl]-3,4-dimethyl-3-cyclohexene carboxylic acid
Melting point: 195° C. (decomposition)
Elemental analysis: for $C_{16}H_{17}NO_3Cl_2$

|  | C | H | N |
|---|---|---|---|
| Calculated (%): | 56.15 | 5.02 | 4.09 |
| Found (%): | 56.19 | 4.85 | 4.41 |

6-(phenyl-aminocarbonyl)-3(4)-methyl-3-cyclohexene carboxylic acid
Melting point: 84°–87° C.
Elemental analysis: for $C_{15}H_{17}NO_3$

|  | C | H | N |
|---|---|---|---|
| Calculated (%): | 69.46 | 6.62 | 5.40 |
| Found (%): | 69.56 | 6.56 | 5.25 |

6-(4-tolylaminocarbonyl)-3(4)-methyl-3-cyclohexene carboxylic acid
Melting point: 135°–137° C.
Elemental analysis: for $C_{16}H_{19}NO_3$

|  | C | H | N |
|---|---|---|---|
| Calculated (%): | 70.29 | 7.02 | 5.12 |
| Found (%): | 70.44 | 6.86 | 5.15 |

6-[(3,5-dimethylphenyl)-aminocarbonyl]-3(4)-methyl-3-cyclohexene carboxylic acid
Melting point: 151°–152° C.
Elemental analysis: for $C_{17}H_{21}NO_3$

|  | C | H | N |
|---|---|---|---|
| Calculated (%): | 71.04 | 7.38 | 4.87 |
| Found (%): | 71.37 | 7.35 | 4.94 |

6-[(4-chlorophenyl)-aminocarbonyl]-3(4)-methyl-3-cyclohexene carboxylic acid
Melting point: 154°–156° C.
Elemental analysis: for $C_{15}H_{16}NO_3Cl$

|  | C | H | N |
|---|---|---|---|
| Calculated (%): | 61.32 | 5.50 | 4.76 |
| Found (%): | 61.41 | 5.53 | 4.90 |

6-[(3-chlorophenyl)-aminocarbonyl]-3(4)-methyl-3-cyclohexene carboxylic acid
Melting point: 162°–163° C. (decomposition)
Elemental analysis: for $C_{15}H_{16}NO_3Cl$

|  | C | H | N |
|---|---|---|---|
| Calculated (%): | 61.32 | 5.50 | 4.76 |
| Found (%): | 61.63 | 5.53 | 4.92 |

6-[(3,5-bistrifluoromethylphenyl)-aminocarbonyl]-3(4)-methyl-3-cyclohexene carboxylic acid Melting point: 159°–160° C.
Elemental analysis: for $C_{17}H_{15}NO_3F_6$

|  | C | H | N |
|---|---|---|---|
| Calculated (%): | 51.64 | 3.83 | 3.54 |
| Found (%): | 51.88 | 3.80 | 3.55 |

6-[(3-trifluoromethylphenyl)-aminocarbonyl]-3(4)-methyl-3-cyclohexene carboxylic acid
Melting point: 160°–162° C. (decomposition)
Elemental analysis: for $C_{16}H_{16}NO_3F_3$

|  | C | H | N |
|---|---|---|---|
| Calculated (%): | 58.70 | 4.93 | 4.28 |
| Found (%): | 58.72 | 4.93 | 4.32 |

6-[(3,5-dichlorophenyl)-aminocarbonyl]-3(4)-methyl-3-cyclohexene carboxylic acid
Melting point: 185°–187° C.
Elemental analysis: for $C_{15}H_{15}NO_3Cl_2$

|  | C | H | N |
|---|---|---|---|
| Calculated (%): | 54.89 | 4.62 | 4.27 |
| Found (%): | 54.85 | 4.62 | 4.42 |

6-[(4-n-propylphenyl)-aminocarbonyl]-3,4-dimethyl-3-cyclohexene carboxylic acid
Melting point: 139°–140° C.
Elemental analysis: for $C_{19}H_{25}NO_3$

|  | C | H | N |
|---|---|---|---|
| Calculated (%): | 72.33 | 8.00 | 4.44 |
| Found (%): | 72.56 | 8.06 | 4.44 |

6-[(4-methoxyphenyl)-aminocarbonyl]-3,4-dimethyl-3-cyclohexene carboxylic acid
Melting point: 131°–132° C.
Elemental analysis: for $C_{17}H_{21}NO_4$

|  | C | H | N |
|---|---|---|---|
| Calculated (%): | 67.29 | 6.99 | 4.61 |
| Found (%): | 67.26 | 6.93 | 4.79 |

6-[(2-chloro-5-trifluoromethylphenyl)-aminocarbonyl]-3,4-dimethyl-3-cyclohexene carboxylic acid
Melting point: 160°–161° C.
Elemental analysis: for $C_{17}H_{17}NO_3ClF_3$

|  | C | H | N |
|---|---|---|---|
| Calculated (%): | 54.32 | 4.56 | 3.72 |
| Found (%): | 54.14 | 4.52 | 3.69 |

6-[(2-methyl-4-chlorophenyl)-aminocarbonyl]-3(4)-methyl-3-cyclohexene carboxylic acid
Melting point: 136°–137.5° C.
Elemental analysis: for $C_{16}H_{18}NO_3Cl$

|  | C | H | N |
|---|---|---|---|
| Calculated (%): | 62.43 | 5.90 | 4.55 |
| Found (%): | 62.52 | 5.88 | 4.52 |

6-[(3-ethylphenyl)-aminocarbonyl]-3(4)-methyl-3-cyclohexene carboxylic acid
Melting point: 134°–135° C.
Elemental analysis: for $C_{17}H_{21}NO_3$

|  | C | H | N |
|---|---|---|---|
| Calculated (%): | 71.04 | 7.38 | 4.87 |
| Found (%): | 70.98 | 7.23 | 4.91 |

6-[(3chlorophenyl)-aminocarbonyl]-3,4-dimethyl-3-cyclohexene carboxylic acid
Melting point: 191° C. (decomposition)
Elemental analysis: for $C_{16}H_{18}NO_3Cl$

|  | C | H | N |
|---|---|---|---|
| Calculated (%): | 62.43 | 5.90 | 4.55 |
| Found (%): | 62.48 | 5.81 | 4.69 |

EXAMPLE 4

N-(phenyl)-4-methyl-4-cyclohexene-1,2-dicarboximide 600 mg of 6-(phenyl aminocarbonyl)-3(4)-methyl-3-cyclohexene carboxylic acid was dehydrated by heating to a temperature of 180° C. for 4 hours, and the product was chromatographied through a silica gel column using a solvent of n-hexane/ethyl acetate (10/1) mixture, and then recrystallized from isopropyl ether to provide 300 mg of the title compound.
Melting point: 92°–93° C.
Elemental analysis: for $C_{15}H_{15}NO_2$

|  | C | H | N |
|---|---|---|---|
| Calculated (%): | 74.65 | 6.27 | 5.80 |
| Found (%): | 74.69 | 6.27 | 5.82 |

EXAMPLE 5

The following compounds were obtained in the same manner as in Example 4. N-(phenyl)-4,5-dimethyl-4-cyclohexene-1,2-dicarboximide
Melting point: 85°–86° C.
Elemental analysis: for $C_{16}H_{17}NO_2$

|  | C | H | N |
|---|---|---|---|
| Calculated (%): | 75.25 | 6.72 | 5.48 |
| Found (%): | 75.45 | 6.71 | 5.53 |

N-(3-chlorophenyl)-4-methyl-4-cyclohexene-1,2-dicarboximide
Melting point: 108°–109° C.
Elemental analysis: for $C_{15}H_{14}NO_2Cl$

|  | C | H | N |
|---|---|---|---|
| Calculated (%): | 65.33 | 5.12 | 5.08 |
| Found (%): | 65.31 | 5.00 | 5.07 |

N-(4-chlorophenyl)-4,5-dimethyl-4-cyclohexene-1,2-dicarboximide
Melting point: 125°–126° C.
Elemental analysis: for $C_{16}H_{16}NO_2Cl$

|  | C | H | N |
|---|---|---|---|
| Calculated (%): | 66.31 | 5.57 | 4.83 |
| Found (%): | 66.32 | 5.58 | 4.82 |

N-(3-trifluoromethylphenyl)-4,5-dimethyl-4-cyclohexene-1,2-dicarboximide
Melting point: 178°–179° C.
Elemental analysis: for $C_{17}H_{16}NO_2F_3$

|  | C | H | N |
|---|---|---|---|
| Calculated (%): | 63.14 | 4.99 | 4.33 |
| Found (%): | 63.23 | 4.92 | 4.24 |

N-(3-trifluoromethylphenyl)-4-methyl-4-cyclohexene-1,2-dicarboximide
Melting point: 145°–146° C.
Elemental analysis: for $C_{16}H_{14}NO_2F_3$

|  | C | H | N |
|---|---|---|---|
| Calculated (%): | 62.12 | 4.57 | 4.52 |
| Found (%): | 62.28 | 4.48 | 4.57 |

N-(3,5-dimethylphenyl)-4-methyl-4-cyclohexene-1,2-dicarboximide
Melting point: 98°–99° C.
Elemental analysis: for $C_{17}H_{19}NO_2$

|  | C | H | N |
|---|---|---|---|
| Calculated (%): | 75.79 | 7.12 | 5.20 |
| Found (%): | 75.81 | 7.15 | 5.18 |

N-(3,5-dimethylphenyl)-4,5-dimethyl-4-cyclohexene-1,2-dicarboximide
Melting point: 122°–123° C.
Elemental analysis: for $C_{18}H_{21}NO_2$

|  | C | H | N |
|---|---|---|---|
| Calculated (%): | 76.28 | 7.48 | 4.94 |
| Found (%): | 76.28 | 7.37 | 4.96 |

N-(3,5-dichlorophenyl)-4-methyl-4-cyclohexene-1,2-dicarboximide
Melting point: 80°–81° C.
Elemental analysis: for $C_{15}H_{13}NO_2Cl_2$

|  | C | H | N |
|---|---|---|---|
| Calculated (%): | 58.07 | 4.23 | 4.51 |
| Found (%): | 58.07 | 4.19 | 4.47 |

N-(3,5-dichlorophenyl)-4,5-dimethyl-4-cyclohexene-1,2-dicarboximide
Melting point: 130°–132° C.
Elemental analysis: for $C_{16}H_{15}NO_2Cl_2$

|  | C | H | N |
|---|---|---|---|
| Calculated (%): | 59.26 | 4.67 | 4.32 |
| Found (%): | 59.13 | 4.57 | 4.29 |

N-(3,5-bistrifluoromethylphenyl)-4-methyl-4-cyclohexene-1,2-dicarboximide
Melting point: 94°–95° C.
Elemental analysis: for $C_{17}H_{13}NO_2F_6$

|  | C | H | N |
|---|---|---|---|
| Calculated (%): | 54.11 | 3.47 | 3.71 |
| Found (%): | 54.39 | 3.55 | 3.65 |

N-(3,5-bistrifluoromethylphenyl)-4,5-dimethyl-4-cyclohexene-1,2-dicarboximide
Melting point: 127°–128° C.
Elemental analysis: for $C_{18}H_{15}NO_2F_6$

|  | C | H | N |
|---|---|---|---|
| Calculated (%): | 55.24 | 3.87 | 3.58 |
| Found (%): | 55.07 | 3.68 | 3.55 |

EXAMPLE 6

6-(phenylaminocarbonyl)-3(4)-methyl-3-cyclohexene sodium carboxylate 2.59 g of 6-(phenylaminocarbonyl)-3(4)-methyl-3-cyclohexene carboxylic acid was dissolved in 10 ml of ethyl alcohol. 0.1N sodium hydroxide solution in ethyl alcohol was added thereto, and the solvent was then distilled off. The product was dried under a reduced pressure to provide 2.62 g of the title compound.
Elemental analysis: for $C_{15}H_{16}NO_3Na \cdot 0.2H_2O$

|  | C | H | N |
|---|---|---|---|
| Calculated (%): | 63.22 | 5.81 | 4.91 |
| Found (%): | 63.19 | 5.87 | 4.64 |

EXAMPLE 7

The following compounds were obtained in the same manner as in Example 6.
6-(phenyl-aminocarbonyl)-3,4-dimethyl-3-cyclohexene sodium carboxylate
Elemental analysis: for $C_{16}H_{18}NO_3Na \cdot 0.1H_2O$

|  | C | H | N |
|---|---|---|---|
| Calculated (%): | 64.66 | 6.18 | 4.71 |
| Found (%): | 64.51 | 6.20 | 4.50 |

6-[(3,5-dimethylphenyl)-aminocarbonyl]-3(4)-methyl-3-cyclohexene sodium carboxylate
Elemental analysis: for $C_{17}H_{20}NO_3Na$

|  | C | H | N |
|---|---|---|---|
| Calculated (%): | 65.99 | 6.52 | 4.52 |
| Found (%): | 65.91 | 6.51 | 4.35 |

6-[(3-chlorophenyl)-aminocarbonyl]-3(4)-methyl-3-cyclohexene sodium carboxylate

Elemental analysis: for $C_{15}H_{15}NO_3ClNa$

|  | C | H | N |
|---|---|---|---|
| Calculated (%): | 57.05 | 4.79 | 4.43 |
| Found (%): | 57.03 | 4.78 | 4.31 |

6-[(4-chlorophenyl)-aminocarbonyl]-3,4-dimethyl-3-cyclohexene sodium carboxylate
Elemental analysis: for $C_{16}H_{17}NO_3ClNa.0.2H_2O$

|  | C | H | N |
|---|---|---|---|
| Calculated (%): | 57.32 | 5.30 | 4.17 |
| Found (%): | 57.58 | 5.29 | 4.04 |

6-[(3,5-bistrifluoromethylphenyl)-aminocarbonyl]-3,4-dimethyl-3-cyclohexene sodium carboxylate
Elemental analysis: for $C_{18}H_{16}NO_3F_6Na.0.8H_2O$

|  | C | H | N |
|---|---|---|---|
| Calculated (%): | 49.29 | 3.86 | 3.19 |
| Found (%): | 49.33 | 3.70 | 3.14 |

6-[(3,5-bistrifluoromethylphenyl)-aminocarbonyl]-3(4)-methyl-3-cyclohexene sodium carboxylate
Elemental analysis: for $C_{17}H_{14}NO_3F_6Na.0.5H_2O$

|  | C | H | N |
|---|---|---|---|
| Calculated (%): | 48.40 | 3.47 | 3.32 |
| Found (%): | 48.35 | 3.45 | 3.27 |

6[(3-trifluoromethylphenyl)-aminocarbonyl]-3(4)-methyl-3-cyclohexene sodium carboxylate
Elemental analysis: for $C_{16}H_{15}NO_3F_3Na.0.5H_2O$

|  | C | H | N |
|---|---|---|---|
| Calculated (%): | 53.62 | 4.50 | 3.90 |
| Found (%): | 53.69 | 4.38 | 3.77 |

6-[(3trifluoromethylphenyl)-aminocarbonyl]-3,4-dimethyl-3-cyclohexene sodium carboxylate
Elemental analysis: for $C_{17}H_{17}NO_3F_3Na.0.4H_2O$

|  | C | H | N |
|---|---|---|---|
| Calculated (%): | 55.09 | 4.58 | 3.78 |
| Found (%): | 55.03 | 4.74 | 3.79 |

6-[(3,5-dichlorophenyl)-aminocarbonyl]-3(4)-methyl-3-cyclohexene sodium carboxylate
Elemental analysis: for $C_{15}H_{14}NO_3Cl_2Na.0.4H_2O$

|  | C | H | N |
|---|---|---|---|
| Calculated (%): | 50.40 | 4.18 | 3.91 |
| Found (%): | 50.43 | 4.15 | 3.88 |

6-[(3,5-dichlorophenyl)-aminocarbonyl]-3,4-dimethyl-3-cyclohexene sodium carboxylate
Elemental analysis: for $C_{16}H_{16}NO_3Cl_2Na$

|  | C | H | N |
|---|---|---|---|
| Calculated (%): | 52.75 | 4.43 | 3.84 |
| Found (%): | 52.60 | 4.54 | 3.75 |

What is claimed is:

1. A compound of the formula:

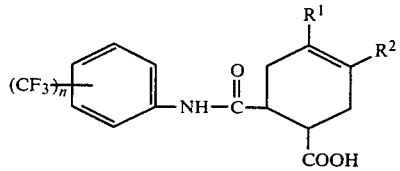

wherein n represents an integer of 1 or 2, $R^1$ and $R^2$ are a hydrogen atom or a methyl group, with the proviso that both $R^1$ and $R^2$ are not hydrogen at the same time, and pharmaceutically acceptable salts thereof.

2. A pharmaceutical composition for treating or preventing diseases associated with convulsion, which comprises a compound according to claim 1 and a pharmaceutically acceptable carrier.

3. A pharmaceutical composition for treating and/or preventing diseases associated with cerebral dysfunction which comprises the compound of claim 1 and a pharmaceutically acceptable carrier.

4. A pharmaceutical composition as claimed in claim 3 wherein the disease associated with cerebral dysfunction is selected from the group consisting of epilepsy, cerebrovascular disease squelae or head injury squelae.

5. A pharmaceutical composition for treating and/or preventing various symptoms associated with a disease selected from the group consisting of epilepsy, cerebrovascular disease squelae or head injury squelea which comprises the compound of claim 1 and a pharmaceutically acceptable carrier.

6. A pharmaceutical composition as claimed in claim 5 wherein the symptom is one or more selected from the group consisting of convulsions, disturbance of consciousness, impaired memory or disturbance of movement.

7. A method for treating and/or preventing a patient afflicted with a disease associated with cerebral dysfunction which comprises administering to said patient a therapeutically effective amount of the compound of claim 1.

8. A method for treating and/or preventing various symptoms associated with a disease selected from the group consisting of epilepsy, cerebrovascular disease squelea or head injury squelea, which comprises administering to a patient having said symptoms, a therapeutically effective amount of the compound of claim 1.

9. A pharmaceutical composition for enhancing the digestive function which composition comprises as an active ingredient, the compound of claim 1 and a pharmaceutically acceptable carrier therefor.

10. 6[(3,5-Bistrifluoromethylphenyl)-aminocarbonyl]-3,4-dimethyl-3-cyclohexene carboxylic acid, or a pharmaceutically acceptable salt thereof, according to claim 1.

11. 6[(3,5-Bistrifluoromethylphenyl)-aminocarbonyl]-3(4)-methyl-3-cyclohexene carboxylic acid, or a pharmaceutically acceptable salt thereof, according to claim 1.

12. A method for enhancing the digestive function in a patient which comprises administering to the patient a therapeutically effective amount of the compound of the formula:

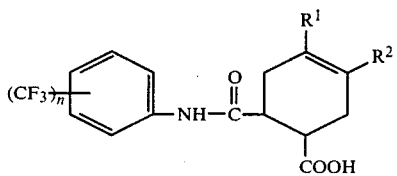

wherein n represents an integer of 1 or 2; and $R^1$ and $R^2$ are hydrogen atom or a methyl group.

13. A pharmaceutical composition for enhancing the digestive function, according to claim 9 which composition comprises as an active ingredient 6-[(3,5-bistrifluoromethylphenyl)-aminocarbonyl]-3,4-dimethyl-3-cyclohexene carboxylic acid or a pharmaceutically acceptable salt thereof.

14. A method for enhancing the digestive function, according to claim 12 which comprises administering a therapeutically effective amount of 6-[(3,5-bistrifluoromethylphenyl)-aminocarbonyl]-3,4-dimethyl-3-cyclohexene carboxylic acid or a pharmaceutically acceptable salt thereof.

15. A pharmaceutical composition for enhancing the digestive function, according to claim 9 which composition comprises as an active ingredient 6-[(3,5-bistrifluoromethyl)-aminocarbonyl]-3(4)-methyl-3-cyclohexene carboxylic acid or a pharmaceutically acceptable salt thereof.

16. A method for enhancing the digestive function, according to claim 12 which comprises administering a therapeutically effective amount of 6-[(3,5-bistirfluoromethyl)-aminocarbonyl]-3(4)-methyl-3-cyclohexene carboxylic acid or a pharmaceutically acceptable salt thereof.

* * * * *